United States Patent
Graves (10) Patent No.: US 11,719,708 B2
(45) Date of Patent: Aug. 8, 2023

(54) DIAGNOSING AND TREATING ALZHEIMER'S DISEASE

(71) Applicant: Brigham Young University, Provo, UT (US)

(72) Inventor: Steven William Graves, Provo, UT (US)

(73) Assignee: Brigham Young University, Provo, UT (US)

( * ) Notice: Subject to any disclaimer, the term of this patent is extended or adjusted under 35 U.S.C. 154(b) by 0 days.

(21) Appl. No.: 16/316,007

(22) PCT Filed: Jul. 6, 2017

(86) PCT No.: PCT/US2017/040992
§ 371 (c)(1),
(2) Date: Jan. 7, 2019

(87) PCT Pub. No.: WO2018/009727
PCT Pub. Date: Jan. 11, 2018

(65) Prior Publication Data
US 2020/0191804 A1 Jun. 18, 2020

Related U.S. Application Data

(60) Provisional application No. 62/359,082, filed on Jul. 6, 2016.

(51) Int. Cl.
*G01N 33/68* (2006.01)
*G01N 33/92* (2006.01)
*A61K 45/06* (2006.01)

(52) U.S. Cl.
CPC ......... *G01N 33/6896* (2013.01); *G01N 33/92* (2013.01); *A61K 45/06* (2013.01); *G01N 2800/2821* (2013.01)

(58) Field of Classification Search
CPC ............... G01N 33/6896; G01N 33/92; G01N 2800/2821; A61K 45/06
See application file for complete search history.

(56) References Cited

U.S. PATENT DOCUMENTS

2006/0172429 A1 8/2006 Nilsson et al.
2006/0228728 A1 10/2006 Cox et al.
2009/0155223 A1 6/2009 Kerr et al.
2009/0318747 A1 12/2009 Fischell et al.
2015/0290460 A1 10/2015 De Riddler

FOREIGN PATENT DOCUMENTS

WO WO 2009/156747 A2 12/2009

OTHER PUBLICATIONS

Anand.; "Discovery of Low-Molecular Weight Novel Serum Biomarkers for Diagnosing Preeclampsia and Alzheimer's Disease." All Theses and Dissertations; BYU Scholars Archive; Mar. 1, 2016; 187 Pages.
Anand et al.; "Discovery and Confirmation of Diagnostic Serum Lipid Biomarkers for Alzheimer's Disease Using Direct Infusion Mass Spectrometry." Journal of Alzheimer's Disease; Diagnostic Serum lipidomic AD Biomarkers; vol. 59; 2017; pp. 277-290.
Han et al.; "Metabolomics in Early Alzheimer's Disease: Identification of Altered Plasma Sphingolipidome Using Shotgun Lipidomics." Lipidomics in Alzheimer's Disease; PLOS One; vol. 6, Issue 7; Jul. 11, 2011; pp. E21643-e21643.
PCT Application No. PCT/US2017/040992, Filing Date Jul. 6, 2017, Steven William Graves, International Search Report, dated Oct. 4, 2017; 10 Pages.
Wood et al.; "Mass Spectrometry Strategies for Clinical Metabolomics and Lipidomics in Psychiatry, Neurology, and Neuro-Oncology." Neuropsychopharmacology Reviews; American College of Neuropsychopharmacology; vol. 39; 2014; pp. 24-33.

*Primary Examiner* — Olga N Chernyshev
(74) *Attorney, Agent, or Firm* — Thorpe North and Western, LLP; Todd B. Alder (57) ABSTRACT

A method of treating a subject having Alzheimer's disease can include assaying a biological medium obtained from the subject for a biomarker selected from the group consisting of Biomarker 1, Biomarker 2, Biomarker 3, Biomarker 4, Biomarker 5, Biomarker 6, Biomarker 7, Biomarker 8, Biomarker 9, Biomarker 10, Biomarker 11, and combinations thereof, where Biomarker 1 has a mass-to-charge ratio (m/z) of 229.13, Biomarker 2 has a m/z of 514.38, Biomarker 3 has a m/z of 602.44, Biomarker 4 has a m/z of 620.42, Biomarker 5 has a m/z of 630.47, Biomarker 6 has a m/z of 703.56, Biomarker 7 has a m/z of 724.52, Biomarker 8 has a m/z of 778.54, Biomarker 9 has a m/z of 799.66, Biomarker 10 has a m/z of 824.60, and Biomarker 11 has a m/z of 842.61. The method can also include relating a characteristic of the biomarker to a presence of Alzheimer's disease in the subject and treating the subject for Alzheimer's disease.

18 Claims, 3 Drawing Sheets

DIAGNOSING AND TREATING ALZHEIMER'S DISEASE

PRIORITY DATA

This application is the National Stage of International Application No. PCT/US2017/040992, filed Jul. 6, 2017, which claims the benefit of U.S. Provisional Patent Application Ser. No. 62/359,082, filed on Jul. 6, 2016, both of which are incorporated herein by reference.

BACKGROUND

Alzheimer's disease (AD) is a debilitating disease for which there is no current cure, which worsens as it progresses, eventually leading to death. Currently there are no generally acceptable biomarkers for AD, and the diagnosis of this condition, while improved, is generally subjective. Often such diagnoses are confirmed late in the disease progression, when damage to neural tissue has limited treatment options. The measurement of amyloid β protein (1-42), tau protein, and phosphorylated tau have been proposed as biomarkers measured in the cerebrospinal fluid (CSF) of symptomatic individuals. These, in conjunction with more sensitive imaging techniques involving the CSF introduction of dyes that target these same proteins, are able to identify some fraction of AD subjects, but not at its earliest stage. These approaches are, however, invasive, expensive, and unfeasible as screening techniques.

BRIEF DESCRIPTION OF THE DRAWINGS

For a fuller understanding of the nature and advantage of the present invention, reference is being made to the following detailed description of preferred embodiments and in connection with the accompanying drawings, in which.

DETAILED DESCRIPTION

Before the present disclosure is described herein, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

Definitions

The following terminology will be used in accordance with the definitions set forth below:

As used herein, the terms "subject" and "individual" can be used interchangeably, and are intended to refer to a human.

In this application, "comprises," "comprising," "containing" and "having" and the like can have the meaning ascribed to them in U.S. patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. patent law. "Consisting essentially of" or "consists essentially of" have the meaning generally ascribed to them by U.S. patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open ended term, like "comprising" or "including," it is understood that direct support should be afforded also to "consisting essentially of" language as well as "consisting of" language as if stated explicitly, and vice versa. Further, it is to be understood that the listing of components, species, or the like in a group is done for the sake of convenience and that such groups should be interpreted not only in their entirety, but also as though each individual member of the group has been articulated separately and individually without the other members of the group unless the context dictates otherwise. This is true of groups contained both in the specification and claims of this application. Additionally, no individual member of a group should be construed as a de facto equivalent of any other member of the same group solely based on their presentation in a common group without indications to the contrary.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

Reference throughout this specification to "an example" or "exemplary" means that a particular feature, structure, or characteristic described in connection with the example is included in at least one embodiment of the present invention. Thus, appearances of the phrases "in an example" or the word "exemplary" in various places throughout this specification are not necessarily all referring to the same embodiment.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

The Disclosure

Alzheimer's disease (AD) is a progressive neurodegenerative disorder and the most common cause of age-related dementia. Currently, as many as 25 million people worldwide may have AD with more than 4 million new cases reported every year. AD is characterized by declining cognitive function including memory, language, motor control, spatial ability, and executive function, and in many individuals an eventual marked change in behavior. General risk factors for AD include age, female sex, and certain genetic backdrops. However, the actual risk of an individual for AD can be challenging to determine. This in turn has limited drug trials and effective treatments.

Several hypotheses exist for AD etiology. The most common theory proposes that increased amyloid β protein (Aβ) deposits, resulting from the cleavage of amyloid precursor protein by β-secretase and γ-secretase, lead to amyloid plaque formation. Another hypothesis proposes the formation of neurofibrillary tangles (NFT) of abnormally phosphorylated tau protein. These tangles are proposed to be the primary pathological event leading to loss of synapses and neurons with the resulting clinical sequelae.

Mild cognitive impairment (MCI) is often a precursor of AD but may be linked to other types of dementia. Thus, it is presently believed in the art that the definite diagnosis of AD can only be made by postmortem histopathological analysis. Further, the clinical diagnosis of AD is still subjective, and is based on prior medical records, lab tests, neuroimaging, and neuropsychological evaluation, including memory tests. Early diagnosis is challenging, although clinical centers specializing in AD appear better able to identify subjects with MCI that will progress to AD; but generally, accuracies are quite variable.

More quantitative methods of AD diagnosis exist, but are not routinely used. For example, a variety of imaging techniques have been employed in the past to aid in AD diagnosis. Specifically, fluoro-deoxyglucose positron emission tomography (FDG-PET) has been used in past studies involving mild AD subjects that measures reduced glucose metabolism due to synaptic loss in brain. Magnetic resonance imaging (MRI) has been used to measure hippocampal volume as an estimation of neuron loss. Positron emission tomography (PET), using ligands such as Pittsburgh compound B ($^{11}C$-PIB) that bind Aβ plaques, has also been extensively studied. A novel ligand (S)-[$^{18}F$]THK5117 that binds to tau aggregates has also been explored. Some of these techniques are quite sensitive but are used almost exclusively in the research setting, due to their clinical complexity, risk, and substantial expense.

Studies of cerebrospinal fluid Aβ and phosphorylated tau have found them to be reasonably accurate for mid to late stage AD, but of limited use in early or very early stage AD. Blood levels of tau protein are below the detection limit for many assays, and measured serum or plasma Aβ peptide has not proved to have consistent diagnostic value for AD. Also, some studies have indicated that there is no correlation between Aβ peptide and the severity of dementia. While there is an increase in AD risk when an individual has the apolipoprotein E ε4 (ApoE4) allele or alleles, Apo E4 genotyping cannot be used as an AD biomarker because of its low predictive value.

As such, there are presently no accepted serologic or radiologic tests to diagnose AD, most especially early stage AD. Imaging using radio-ligands is promising and shows good results for many with AD, but it is expensive, time consuming, and invasive. Still, many who investigate this disease believe that neurodegeneration in AD begins long before the appearance of clinical symptoms. These early changes likely involve molecular changes, and as such, there is a reasonable presumption that very early AD can be identified and tracked via testing blood for the presence of markers signifying such molecular changes.

Thus, the early diagnosis of AD remains challenging and some may question the value of having an early diagnosis when effective treatment options are limited. However, most concede that drugs are unlikely to provide a substantial benefit in advanced AD. Such drugs may, however, provide a substantial benefit if administered prior to neural degeneration. Consequently, it seems valuable that a method be available to diagnose early AD to allow for drug development and evaluation. Therefore, there is an unmet need to find serum biomarkers for AD, especially for very early stage disease. Moreover, there is an unmet need to develop diagnostics for future risk of AD, rates of AD progression, and responsiveness to therapies. The present disclosure describes novel methods and biomarkers that help to remedy these deficiencies. Further, the present methods and biomarkers can, in some cases, be coupled with one or more treatment regimens for AD, such as early stage AD, for example, as well as methods for providing treatment to AD prior to a subject showing outward signs of AD.

In further detail, lipids can play participative role in disease. For example, lipids are frequently modified as a consequence of particular disease states, but they can also to occasionally act as mediators of disease. In AD, neurodegeneration, a key feature of AD, leads to the breakdown of cell membranes, resulting in abnormal abundances of membrane lipids. There is evidence of oxidative stress in brains of AD subjects, and thus it is possible that continuous oxidative stress can lead to accumulation of oxidized lipid species, such as isoprostanes or malondialdehyde, for example. It is also noted that alterations in ceramides can be seen at different stages of AD. Additionally, the breakdown of phosphatidylcholines can also be an indicator of neurodegeneration.

The 'global' characterization of alterations in the serum lipidome between AD cases and controls can reveal biomarkers for diagnosis of AD, even early AD. The present disclosure has utilized a novel serum lipidomic approach to elucidate serum biomarkers and biomarker combinations that are linked to AD, including those capable of identifying very early stage AD. A serum lipidomic study (Biomarker Study, below) was performed to discover novel molecular biomarkers that were quantitatively different between subjects with AD and age, gender, and ApoE4 matched controls, and thus could potentially be used in determining the presence and/or stage of AD in a subject. Additionally, serum was utilized as the biological medium for the discovery of the biomarkers, thus allowing for easy and inexpensive specimen acquisition in assays developed to screen for such biomarkers. It is noted, however, that the present scope is not limited to serum, and such biomarkers can be assayed for using any biological medium.

In some examples, one or more of biomarkers can be utilized in the determination of AD in a subject, or the risk factors of a subject for AD. In other examples, one or more of the biomarkers can diagnose the presence or absence of AD in a subject. In yet other examples, the one or more biomarkers can determine the stage of AD in a subject, such as very early stage AD (e.g. clinical dementia ratings (CDR) 0.5 or CDR 1), for example. In other examples, one or more biomarkers can be used to diagnose the absence of AD in a subject. In yet other examples, the presence or serum level of one or more biomarkers can be detected, and the presence or serum level can be quantified against a standard or control to determine the presence of, or the risk of developing, AD. Through the early detection of AD, or the risk of developing AD, treatment can be initiated prior to the onset of the physical symptoms relating to the neural degeneration, thus providing the unique opportunity to treat or otherwise control this devastating disease before a subject experiences irreversible cognitive loss, or before a subject experiences further irreversible cognitive loss.

Accordingly, in one example, a method of determining the presence of Alzheimer's disease in a subject can include detecting, in a biological medium obtained from the subject, a characteristic of one or more biomarkers shown in Table 6 (i.e. Biomarker 1, Biomarker 2, Biomarker 3, Biomarker 4, Biomarker 5, Biomarker 6, Biomarker 7, Biomarker 8, Biomarker 9, Biomarker 10, Biomarker 11), where Biomarker 1 has a mass-to-charge ratio (m/z) of 229.13, Biomarker 2 has a m/z of 514.38, Biomarker 3 has a m/z of 602.44, Biomarker 4 has a m/z of 620.42, Biomarker 5 has a m/z of 630.47, Biomarker 6 has a m/z of 703.56, Biomarker 7 has a m/z of 724.52, Biomarker 8 has a m/z of 778.54, Biomarker 9 has a m/z of 799.66, Biomarker 10 has a m/z of 824.60, and Biomarker 11 has a m/z of 842.61. Thus, a characteristic of the biomarker, such as the presence, absence, increase as compared to a control value, and/or decrease as compared to a control value of the one or more biomarkers in the subject, can be diagnostic of the presence of AD and/or a particular stage of AD. In some cases, whether the presence, absence, increase in a level of the biomarker as compared to a control value, and/or decrease in a level of the biomarker as compared to a control value is measured can depend on the particular analytical instrumentation employed. For example, in some cases, a mass spectrometer can have much greater sensitivity for some analytes than an evaporative light scattering detector or a flame ionization detector, for example. Thus, in some cases, one analytical method may only be able to detect the presence and/or absence of a particular analyte, whereas other analytical methods may be able to quantify an amount of the analyte. In some cases, this can be contingent on the limit of detection (LOD) or limit of quantitation (LOQ) of a particular method.

In some examples, a method for diagnosing AD and/or treating a subject having AD, can include detecting, in a biological medium obtained from the subject, a characteristic of one or more biomarkers shown in Table 6. Thus, the presence, absence, increase as compared to a control value, and/or decrease as compared to a control value of the two or more biomarkers in the individual can be diagnostic of AD and/or a particular stage of AD. In another example, the biological medium is assayed for three or more of Biomarkers 1-11. In yet another example, the biological medium is assayed for four or more of Biomarkers 1-11. In yet another example, the biological medium is assayed for five or more of Biomarkers 1-11. In yet another example, the biological medium is assayed for six or more of Biomarkers 1-11. In yet another example, the biological medium is assayed for seven or more of Biomarkers 1-11. In yet another example, the biological medium is assayed for eight or more of Biomarkers 1-11. In yet another example, the biological medium is assayed for nine or more of Biomarkers 1-11. In yet another example, the biological medium is assayed for ten or more of Biomarkers 1-11. In yet another example, the biological medium is assayed for each of Biomarkers 1-11.

In a further example, the biological medium can be assayed for Biomarker 1. In some examples, Biomarker 1 can be assayed in combination with one or more of Biomarkers 2-11. In another example, the biological medium can be assayed for Biomarker 2. In some examples, Biomarker 2 can be assayed in combination with one or more of Biomarker 1 and Biomarkers 3-11. In another example, the biological medium can be assayed for Biomarker 3. In some examples, Biomarker 3 can be assayed in combination with one or more of Biomarker 1, Biomarker 2, and Biomarkers 4-11. In another example, the biological medium can be assayed for Biomarker 4. In some examples, Biomarker 4 can be assayed in combination with one or more of Biomarkers 1-3 and Biomarkers 5-11. In another example, the biological medium can be assayed for Biomarker 5. In some examples, Biomarker 5 can be assayed in combination with one or more of Biomarkers 1-4 and Biomarkers 6-11. In another example, the biological medium can be assayed for Biomarker 6. In some examples, Biomarker 6 can be assayed in combination with one or more of Biomarkers 1-5 and Biomarkers 7-11. In another example, the biological medium can be assayed for Biomarker 7. In some examples, Biomarker 7 can be assayed in combination with one or more of Biomarkers 1-6 and Biomarkers 8-11. In another example, the biological medium can be assayed for Biomarker 8. In some examples, Biomarker 8 can be assayed in combination with one or more of Biomarkers 1-7 and Biomarkers 9-11. In another example, the biological medium can be assayed for Biomarker 9. In some examples, Biomarker 9 can be assayed in combination with one or more of Biomarkers 1-8, Biomarker 10, and Biomarker 11. In another example, the biological medium can be assayed for Biomarker 10. In some examples, Biomarker 10 can be assayed in combination with one or more of Biomarkers 1-9 and Biomarker 11. In another example, the biological medium can be assayed for Biomarker 11. In some examples, Biomarker 11 can be assayed in combination with one or more of Biomarkers 1-10.

It is thus to be understood that the present scope includes assaying all combinations of Biomarkers 1-11 as any of a number of biomarker panels, including all pairs of biomarkers, all combinations of 3 biomarkers, all combinations of 4 biomarkers, all combinations of 5 biomarkers, all combinations of 6 biomarkers, all combinations of 7 biomarkers, all combinations of 8 biomarkers, all combinations of 9 biomarkers, all combinations of 10 biomarkers, and all 11 biomarkers together. Furthermore, a biomarker panel can consist of any number of biomarkers from Biomarker 1-11, all combinations of biomarker pairs, all combinations of 3 biomarkers, all combinations of 4 biomarkers, all combinations of 5 biomarkers, all combinations of 6 biomarkers, all combinations of 7 biomarkers, all combinations of 8 biomarkers, all combinations of 9 biomarkers, all combinations of 10 biomarkers, and all 11 biomarkers together. Such biomarker panels represent novel collections of biomarkers that can be used to detect AD in a subject.

In some examples, the method can further include assaying one or more of Biomarker 12, Biomarker 13, Biomarker 14, Biomarker 16, and Biomarker 17, where Biomarker 12 has a m/z of 430.4, Biomarker 13 has a m/z of 610.5, Biomarker 14 has a m/z of 714.6, Biomarker 15 has a m/z of 766.6, Biomarker 16 has a m/z of 850.8, and Biomarker 17 has a m/z of 864.6 (See Table 4). In some specific examples, the method can include assaying Biomarker 12. In some additional examples, the method can include assaying Biomarker 13. In some additional examples, the method can include assaying Biomarker 14. In yet additional examples, the method can include assaying Biomarker 15. In yet additional examples, the method can include assaying Biomarker 16. In still additional examples, the method can include assaying Biomarker 17.

In some examples, the particular biomarker panel selected can have an Area Under a Receiver Operating Characteristic (ROC) Curve (AUC) for AD or a particular stage of AD of greater than or equal to 0.80. In other examples, the biomarker panel can have an AUC for AD or a particular stage of AD of greater than or equal to 0.85. In yet other examples, the biomarker panel can have an AUC value for AD or a particular stage of AD of greater than or equal to 0.90. As will be appreciated by one skilled in the art, an AUC value is a measurement of how accurately a test separates the test group into those with and without the disease in question. Briefly, the closer the AUC value is to 1 the better the test is at distinguishing between those with and without the disease, whereas the closer the AUC value is to 0.5 the worse the test is at distinguishing those with and without the disease.

Additionally, the method can have good sensitivity and/or specificity. In further detail, with the various samples that are tested, the test can provide four different outcomes: True Positive (a), False Negative (b), False Positive (c), or True Negative (d). Sensitivity is a measure of the probability that a test result will be positive when the disease is present ($a/(a+b)$). Specificity is a measure of the probability that the test result will be negative when the disease is not present ($d/(c+d)$).

With this in mind, in some examples, the method can have a sensitivity for AD or a particular stage of AD of greater than or equal to 0.8, 0.85, 0.9, or 0.95. Additionally, in some examples, the method can have a specificity for AD or a particular stage of AD of greater than or equal to 0.7, 0.75, 0.8, 0.85, or 0.9.

It is additionally noted that, while m/z values are used to identify Biomarkers 1-11 in some examples, any distinguishing characteristic of a biomarker can be utilized, either in addition to or as an alternative for the m/z values. Furthermore, the description of each biomarker by m/z value is for convenience, and should not be construed as an indication that an assay need necessarily utilize MS. Rather, any type of diagnostic technique, device, system, etc., capable of identifying any of the biomarkers in a biological medium is considered to be within the present scope. For example, in some cases, one or more of Biomarkers 1-11 can be assayed by introducing the sample (and associated standards, controls, blanks, etc.) into a separations module, such as a liquid chromatography separations module or a gas chromatography separations module. Further, in some examples, the separations module can be fluidly connected or associated with a suitable detector to detect one or more of Biomarkers 1-11 in the sample. Any suitable detector can be employed. In such cases, one or more of Biomarkers 1-11 can be identified by retention time alone. In other examples, Biomarkers 1-11 can be identified by retention time in combination with m/z or any other suitable property of the biomarker.

However, in some examples MS can be useful in an assay for determining the presence, absence, or level of any of the biomarkers in the biological medium. In some cases, therefore, the method can further include assaying the biological medium using MS for at least one of the biomarkers. It is noted that a variety of MS techniques and MS systems and system configurations can be utilized, all of which are within the present scope. As one example, tandem MS (MS/MS or $MS^2$) can be utilized. In other examples, a single mass spectrometer can be employed. In some examples, the mass spectrometer can be a time-of-flight (TOF) instrument. In some examples, this can include an MS detector that is not a TOF instrument. In another example, Selected Reaction Monitoring (SRM) can be useful. In another example, Multiple Reaction Monitoring (MRM) can be employed. In another yet another example, chromatographic separation by any of several separation methods coupled to a MS system or used in conjunction with a MS can be considered, e.g. nano-liquid chromatography coupled to a MS instrument or two dimensional liquid chromatography coupled to MS.

Other types of assays can additionally be used, either in conjunction with or as a replacement to a MS procedure. The other type of assay can be used as a confirmation of a biomarker identified by MS, or as a stand-alone assay in the identification of one or more biomarker. In one aspect, for example, any assay that can be utilized to detect a glycerophosphatidylcholine or an oxidized glycerophosphatidylcholine is considered to be within the present scope.

Regarding the biological material being assayed, the biological medium can be any biological component of the subject that can include any of the biomarkers of interest. Such can include any tissue, liquefied tissue, bodily fluid, excretion, secretion, and the like. In one example, the biological medium can be a biological fluid. Examples can include whole blood, serum, plasma, urine, lymph, cerebrospinal fluid (CSF), and the like. In one specific example the biological fluid can be serum.

Once a subject has been diagnosed with AD, or a particular stage of AD, an appropriate treatment regimen can be established for the subject. In some examples, a particular type of medication can be administered to the subject. In some examples, the subject can be administered a cholinesterase inhibitor, such as donepezil, rivastigmine, galantamine, the like, or a combination thereof. Cholinsterase inhibitors typically work to prevent the breakdown of acetylcholine. In some cases, this can delay the worsening of symptoms and can be very useful in early to moderate stages of AD (e.g. CDR 0.5-1). However, cholinesterase inhibitors can also be administered to late stage AD subjects as well.

In some examples, memantine can be administered to the subject. Memantine can help regulate the activity of glutamate, which can also delay worsening of symptoms for some subjects. Typically, memantine can be administered to subjects with moderate to late stage AD (e.g. CDR 1-2). In some examples, memantine can be administered to the subject in conjunction with a cholinesterase inhibitor.

In some examples, an anti-amyloid beta antibody (i.e. an antibody that acts against amyloid beta), such as aducanumab, bapineuzumab, solanezumab, the like, or a combination thereof, can be administered to the subject. In some examples, an antitau antibody, such as HJ8.5 or the like, can be administered to the subject. It is also noted that any suitable combination of therapeutics mentioned herein can also be administered to the subject.

In some further examples, the subject can be treated with neurostimulation. Neurostimulation can include deep brain stimulation, transcranial magnetic stimulation, transcranial direct-current stimulation, the like, or combinations thereof. In some examples, neurostimulation can be used in combination with medical treatments, such as those described above.

A biomarker tool for diagnosing or determining risk factors for Alzheimer's disease in a subject is also described herein. In some examples, the biomarker tool can include a biomarker panel having Biomarker 1, Biomarker 2, Biomarker 3, Biomarker 4, Biomarker 5, Biomarker 6, Biomarker 7, Biomarker 8, Biomarker 9, Biomarker 10, Biomarker 11, or a combination thereof. In some examples, the biomarker panel can include two or more biomarkers selected from the group consisting of Biomarker 1, Biomarker 2, Biomarker 3, Biomarker 4, Biomarker 5, Biomarker 6, Biomarker 7, Biomarker 8, Biomarker 9, Biomarker 10, and Biomarker 11. In some additional examples, the biomarker panel can include five or more biomarkers selected from the group consisting of Biomarker 1, Biomarker 2, Biomarker 3, Biomarker 4, Biomarker 5, Biomarker 6, Biomarker 7, Biomarker 8, Biomarker 9, Biomarker 10, and Biomarker 11. In yet other examples, the biomarker panel can include each of Biomarker 1, Biomarker 2, Biomarker 3, Biomarker 4, Biomarker 5, Biomarker 6, Biomarker 7, Biomarker 8, Biomarker 9, Biomarker 10, and Biomarker 11.

In some specific examples, the biomarker panel can consist of two or more, three or more, four or more, five or more, six or more, seven or more, eight or more, nine or more, ten or more, or each of the biomarkers selected from the group consisting of Biomarker 1, Biomarker 2, Biomarker 3, Biomarker 4, Biomarker 5, Biomarker 6, Biomarker 7, Biomarker 8, Biomarker 9, Biomarker 10, and Biomarker 11.

In some specific examples, the biomarker panel can include Biomarker 1. In some additional examples, the biomarker panel can include Biomarker 2. In some additional examples, the biomarker panel can include Biomarker 3. In yet additional examples, the biomarker panel can include Biomarker 4. In yet additional examples, the biomarker panel can include Biomarker 5. In still additional examples, the biomarker panel can include Biomarker 6. In some further examples, the biomarker panel can include Biomarker 7. In some additional examples, the biomarker panel can include Biomarker 8. In some additional examples, the biomarker panel can include Biomarker 9. In yet additional examples, the biomarker panel can include Biomarker 10. In still additional examples, the biomarker panel can include Biomarker 11.

In some examples, the biomarker panel can include Biomarker 1, Biomarker 2, Biomarker 3, Biomarker 4, and Biomarker 8. In some additional examples, the biomarker panel can include Biomarker 2, Biomarker 3, Biomarker 4, Biomarker 5, Biomarker 8, and Biomarker 10. In yet other examples, the biomarker panel can include Biomarker 2, Biomarker 3, Biomarker 4, Biomarker 7, and Biomarker 10. In yet other examples, the biomarker panel can include Biomarker 1, Biomarker 2, Biomarker 4, Biomarker 5, Biomarker 8, and Biomarker 10. In yet other examples, the biomarker panel can include Biomarker 1, Biomarker 2, Biomarker 3, Biomarker 4, Biomarker 5, Biomarker 8, Biomarker 9, and Biomarker 10.

In some examples, the biomarker panel can further include one or more of Biomarker 12, Biomarker 13, Biomarker 14, Biomarker 16, and Biomarker 17, where Biomarker 12 has a m/z of 430.4, Biomarker 13 has a m/z of 610.5, Biomarker 14 has a m/z of 714.6, Biomarker 15 has a m/z of 766.6, Biomarker 16 has a m/z of 850.8, and Biomarker 17 has a m/z of 864.6. In some specific examples, the biomarker panel can include Biomarker 12. In some additional examples, the biomarker panel can include Biomarker 13. In some additional examples, the biomarker panel can include Biomarker 14. In yet additional examples, the biomarker panel can include Biomarker 15. In yet additional examples, the biomarker panel can include Biomarker 16. In still additional examples, the biomarker panel can include Biomarker 17.

Biomarker Study

The following study is one example of obtaining a number of potential AD biomarkers and generating potentially useful multi-marker panels from subject samples. It should be understood that this is merely one approach, and that the methodologies, techniques, and results should not be seen as limiting to the overall scope of the disclosure. Collectively, the results of the Biomarker Study suggest that useful serum lipid biomarkers allow for the accurate diagnosis of most subjects with AD, regardless of stage. Moreover, the majority of these biomarkers were found to be relevant lipid species whose altered expression is consistent with pathologies associated with and in some cases potentially contributing to AD pathology. These are novel, previously undescribed lipid biomarkers for AD and hold out diagnostic promise for subjects with AD, including early stage disease. Further, they can allow for staging of the disease. As such, they can help in identifying individuals with early AD events and provide a tool for easier and more rational selection of therapies and treatment options for individuals at a particular stage of AD.

Study Population

The serum specimens were obtained from the Knight Alzheimer's Disease Research Center (Knight ADRC) at the Washington University School of Medicine, St. Louis, Mo. The study was approved by Institutional Review Boards (IRB) at both the Knight ADRC and Brigham Young University (BYU) for specimen analysis.

In an initial discovery study, sera from 29 cases and 32 controls were analyzed. AD cases included subjects having different stages of AD as indicated by differing clinical dementia ratings (CDR). Cases included 10 subjects with mild cognitive impairment (MCI), also termed very mild AD (CDR 0.5), 10 with mild AD (CDR 1) and 9 with moderate AD (CDR 2). The confirmatory study included 27 cases and 30 controls. AD cases included 9 subjects with CDR 0.5, 9 with CDR 1, and 9 with CDR 2. The demographics of the subjects whose samples were used for the discovery and confirmatory studies are summarized in Tables 1A and 1B. Cases and controls excluded subjects with co-morbidities including thyroid disease, diabetes, etc. Blood specimens, after collection, were allowed to clot at room temperature for 30 minutes followed by separation of serum, removal, and aliquoting of sera with immediate freezing. Serum specimens were maintained frozen at −80° C. until used in these studies.

TABLE 1A

AD demographics for the discovery set of samples

| | No. | | Age (mean) | Apo E status |
|---|---|---|---|---|
| CASES | 29 | 18/29 F, 11/29 M | 79.7 ± 6.6 | Allele 4 positive - 20 Allele 4 negative - 9 |

TABLE 1A-continued

AD demographics for the discovery set of samples

|  | No. |  | Age (mean) | Apo E status |
|---|---|---|---|---|
| CONTROLS | 32 | 18/32 F, 14/32 M | 78.1 ± 6.3 | Allele 4 positive - 7<br>Allele 4 negative - 25 |

TABLE 1B

AD demographics for the confirmatory set of samples

|  | No. |  | Age (mean) | Apo E status |
|---|---|---|---|---|
| CASES | 27 | 16/27 F, 11/27 M | 79.6 ± 8.5 | Allele 4 positive - 14<br>Allele 4 negative - 13 |
| CONTROLS | 30 | 12/30 F, 18/30 M | 77.2 ± 6.2 | Allele 4 positive - 12<br>Allele 4 negative - 18 |

Sample Preparation

Lipid extraction from serum was accomplished as follows: To 200 µL of serum, 1.8 mL of a mixture of hexane and isopropanol (3:2, v:v) and 300 µL of 0.5 M $KH_2PO_4$ were added to a glass tube followed by vigorous vortexing. The stoppered tubes were further mixed on a motorized shaker at room temperature for 1 hour at 80 rpm. To enhance phase separation, 150 µL of water was added and the samples were then centrifuged at 2000 rpm for 12 min. The upper organic phase containing the lipids was collected and dried under nitrogen. Dried lipid samples were redissolved in 200 µL of chloroform:methanol (3:1) and stored at −80° C. until MS analysis.

Mass Spectrometric Analysis of the Lipid Extract

To a 20 µL aliquot of the sample extract, 23 µL of chloroform, 46 µL of methanol and 14 µL of 12 µM ammonium acetate were added and mixed. The samples were directly injected or infused into the mass spectrometer (6530 LC/MS ESI-QTOF, Agilent Technologies, Santa Clara, Calif.) through an electrospray ionization (ESI) source operated in the positive ion mode. A syringe pump was utilized to inject samples at the flow rate of 10 µL/min for 4 min. The ESI source used a standard spray needle having an i.d. of 120 µm. The capillary voltage was set at 3500 V. MS data was collected from mass to charge ratios (m/z) of 100-3000 with an acquisition rate of 1 spectrum/sec. The nebulizer gas and drying gas parameters were optimized to obtain a stable flow. The drying gas was set to 5 L/min at 325° C. with a nebulization gas pressure of 1.03 bar. Agilent Mass Hunter-Qualitative software was used for data analysis. Each specimen generated a mass spectrum from m/z 100 to 3000 from the total ion chromatogram (TIC). A peak list having m/z values for all peaks with their abundances was generated from the mass spectrum.

To reduce analytical variability all MS peaks were normalized. For normalization, 7 abundant peaks representing different classes of lipids were chosen as a reference set. The sum of the intensities (ion counts) of these 7 peaks was used for normalizing all the peaks across the mass spectrum.

For the confirmatory study, all the samples were processed and directly infused into the instrument using the same method at a flow rate of 10 µL/min for 5 minutes (the change being due to a somewhat larger diameter spray needle employed to reduce blockage of the ESI needle). All other parameters were kept identical. All the candidate markers significant in the initial discovery set were reanalyzed for their performance in the second confirmation set.

Chemical Characterization of the Replicating Lipid Biomarkers by Tandem MS

Tandem MS studies were performed on all 35 replicating lipid AD biomarkers. Fragmentation was accomplished using collision-induced dissociation (CID) on an ESI-quadrupole-TOFMS. Both a QSTAR Pulsar 1 quadrupole (Applied Biosystems (Thermo Fisher), Foster City, Calif.) and an Agilent 6530 Q-TOF MS were employed using the positive ion mode.

For the QSTAR, the capillary voltage was set to 4200 V. Samples were injected directly at a flow rate of 2 µL/min and a specific precursor ion targeted in the quadrupole. A spectral acquisition rate of 1 spectrum/sec was used. Focusing and declustering potentials were set to 290 V and 65 V. CID was performed using nitrogen or argon gas. In order to obtain more complete fragmentation coverage, multiple fragmentation energies were used. MS/MS spectra were collected for 2 min. The (multi-channel analyzer function was used to sum all 120 MS/MS spectra and this resulted in higher signal to noise.

For the Agilent 6530, samples were injected at the flow rate of 10 µL/min with the capillary voltage set to 3500 V. The drying gas flow rate and the temperature were 5 L/min and 300° C. MS/MS spectra were collected from m/z 50-3000 at a rate of 1 spectrum/second. Collision energies were optimized to obtain maximum fragmentation coverage. Individual scans were summed using the Add feature of the Mass Hunter program to improve the signal to noise. The targeted MS/MS mode was used to select and fragment the parent ion of interest. The resolution was set to narrow with 1.3 m/z range.

Exact mass studies were accomplished by reference to a set of internal standards added to each specimen. An online database (lipidmaps.org) was used to tentatively determine all the possible lipid species from different classes for a particular parent peak of particular mass. Furthermore, product ions, neutral fragment losses, fragmentation patterns and exact masses of parent and daughter ions were evaluated and where possible compared with experimentally observed fragmentation patterns or with in silico predicted fragmentations to clarify the classes and composition of the markers. Such chemical characterization then may lead to insights into AD related biology.

Statistical Analyses

All normalized monoisotopic peaks with an ion count >150 (~2,000) were subjected to a two-tailed Student's t-test. Peaks having a p-value <0.05 in the first study were further evaluated in a second, independent, confirmatory study. The markers that continued to show p-values <0.05 in the second confirmatory set were then considered candidates and used for biomarker panel development. In addition to peaks having p-values <0.05 being considered, species with p-values <0.10 were also considered for multi-marker modeling recognizing that they might identify more specifically subgroups of subjects within the broader diagnosis and hence be complementary.

Using these replicating markers that continued to show quantitative differences in the second study, statistical modeling was used to combine markers into multi-marker sets with improved diagnostic ability. A variety of binary classification models were evaluated. Of those, a Bayesian Lasso Probit Regression model, which aids in the selection of the most important markers, performed best (R software and packages were used). The approach was applied to just those biomarkers that replicated in the confirmatory study and sets modeled to improve classification correctness. Four binary classification models were developed, comparing controls to all AD cases, then controls versus those AD cases with a CDR of 0.5, then controls versus cases with a CDR of 1, and finally controls versus cases with a CDR of 2. This has been the accepted statistical approach to finding high performing multi-marker panels.

A further type of analysis was carried out that evaluated markers changing progressively with AD disease stage. The binary classification models demonstrated some markers that appeared useful in distinguishing between control samples and samples at a particular stage of AD. Binary models do not provide substantial information about markers that distinguish between different disease stages. To assess this, a Bayesian Lasso Probit Ordinal Regression model, with n-fold cross validation, was used.

Additionally, a far more conservative statistical approach was carried out that predicts the future performance of biomarkers. This employed a Bayesian Lasso Probit Regression analysis with 10-fold internal cross validation. The threshold used to determine classifications in this cross validation study was 0.44, which was found to be optimal in cross validation.

Discovery of Candidate Serum Lipid AD Diagnostic Biomarkers

The first study of 29 cases and 32 controls was used to discover potential biomarkers for all subjects with AD regardless of stage. The approach yielded 89 lipids of interest, displaying quantitative differences between cases and controls, as part of this discovery set. These are summarized in Table 2.

TABLE 2

Candidate AD lipid biomarkers from discovery study.

| m/z | P value | Higher in |
|---|---|---|
| 228.2 | 0.06 | Controls |
| 229.1 | 0.10 | Controls |
| 243.2 | 0.004 | Controls |
| 281.1 | $2.6 \times 10^{-5}$ | Controls |
| 282.2 | $8.8 \times 10^{-5}$ | Controls |
| 280.9 | 0.04 | Controls |
| 295.1 | $6.7 \times 10^{-5}$ | Controls |
| 371.35 | 0.001 | Controls |
| 387.17 | 0.04 | Cases |
| 391.17 | 0.009 | Controls |
| 415.2 | $2.3 \times 10^{-5}$ | Controls |
| 430.3 | 0.03 | Cases |
| 432.2 | $2.6 \times 10^{-5}$ | Controls |
| 437.1 | 0.01 | Controls |
| 447.3 | $2.2 \times 10^{-10}$ | Cases |
| 453.1 | 0.07 | Cases |
| 463.3 | 0.02 | Cases |
| 488.3 | 0.004 | Controls |
| 496.3 | $1.1 \times 10^{-6}$ | Cases |
| 514.4 | 0.01 | Cases |
| 520.3 | 0.0004 | Cases |
| 522.3 | $5.4 \times 10^{-6}$ | Cases |
| 524.3 | $2.7 \times 10^{-5}$ | Cases |
| 577.5 | 0.008 | Cases |
| 579.5 | 0.001 | Cases |
| 601.5 | 0.04 | Cases |
| 602.4 | 0.02 | Cases |
| 603.5 | 0.01 | Cases |
| 610.5 | 0.05 | Cases |
| 611.3 | 0.1 | Cases |
| 614.5 | 0.07 | Controls |
| 616.4 | 0.08 | Controls |
| 620.4 | 0.004 | Controls |
| 627.4 | 0.07 | Cases |
| 630.5 | 0.03 | Cases |
| 639.4 | 0.03 | Cases |
| 640.6 | 0.0001 | Controls |
| 642.6 | $5.3 \times 10^{-9}$ | Controls |

TABLE 2-continued

Candidate AD lipid biomarkers from discovery study.

| m/z | P value | Higher in |
|---|---|---|
| 654.3 | $7.4 \times 10^{-7}$ | Controls |
| 664.6 | 0.1 | Controls |
| 666.9 | 0.01 | Controls |
| 669.6 | $4.4 \times 10^{-6}$ | Controls |
| 671.6 | 0.005 | Controls |
| 688.6 | 0.01 | Controls |
| 701.5 | 0.008 | Controls |
| 703.5 | 0.02 | Controls |
| 714.6 | 0.07 | Controls |
| 717.5 | 0.06 | Controls |
| 724.5 | 0.0007 | Controls |
| 727.5 | $2.3 \times 10^{-10}$ | Cases |
| 729.6 | $3.6 \times 10^{-8}$ | Cases |
| 731.6 | 0.04 | Controls |
| 742.6 | 0.07 | Controls |
| 744.6 | 0.04 | Controls |
| 750.5 | $4 \times 10^{-5}$ | Controls |
| 752.5 | 0.001 | Controls |
| 754.5 | 0.03 | Controls |
| 759.1 | 0.007 | Controls |
| 760.8 | 0.09 | Controls |
| 760.9 | 0.08 | Controls |
| 761.1 | 0.08 | Controls |
| 766.6 | 0.02 | Controls |
| 768.6 | 0.0008 | Controls |
| 778.5 | 0.005 | Controls |
| 786.6 | 0.02 | Controls |
| 792.6 | 0.005 | Controls |
| 794.6 | 0.02 | Controls |
| 799.6 | 0.1 | Controls |
| 810.8 | 0.02 | Controls |
| 812.6 | 0.07 | Controls |
| 820.7 | 0.07 | Cases |
| 822.7 | 0.03 | Cases |
| 824.6 | 0.02 | Cases |
| 842.6 | 0.02 | Cases |
| 844.7 | 0.06 | Controls |
| 846.7 | 0.01 | Cases |
| 848.7 | 0.02 | Cases |
| 850.7 | 0.03 | Cases |
| 860.7 | 0.01 | Cases |
| 862.7 | 0.007 | Cases |
| 864.6 | 0.003 | Cases |
| 881.7 | 0.0005 | Cases |
| 886.7 | 0.02 | Cases |
| 888.8 | 0.01 | Cases |
| 890.8 | 0.01 | Cases |
| 907.8 | 0.009 | Cases |
| 912.7 | 0.005 | Cases |
| 915.8 | $2.3 \times 10^{-5}$ | Cases |
| 930.8 | 0.01 | Cases |

Confirmation of Candidate AD Biomarkers from the First Study

A confirmatory study was conducted to evaluate the performance of the 89 previously discovered lipid markers in a new set of samples. This new study involved serum from 27 AD cases and 30 controls. Of the 89 markers, 35 continued to show statistically significant or near significant p-values between AD cases and controls. These diagnostic biomarker candidates are listed in Table 3.

TABLE 3

Potential markers from Table 2 that were also statistically significant in the confirmatory study

| Exact mass | P value in first discovery | P value in confirmatory | Higher in |
|---|---|---|---|
| 229.14 | 0.1 | 0.003 | Controls |
| 430.38 | 0.03 | 0.001 | Cases |
| 488.39 | 0.004 | 0.09 | Controls |

TABLE 3-continued

Potential markers from Table 2 that were also statistically significant in the confirmatory study

| Exact mass | P value in first discovery | P value in confirmatory | Higher in |
|---|---|---|---|
| 496.33 | $10^{-5}$ | 0.06 | Cases |
| 514.38 | 0.01 | 0.01 | Cases |
| 522.35 | $10^{-6}$ | 0.02 | Cases |
| 577.51 | 0.008 | 0.009 | Cases |
| 601.52 | 0.04 | 0.02 | Cases |
| 603.53 | 0.02 | 0.003 | Cases |
| 602.44 | 0.02 | 0.006 | Cases |
| 610.53 | 0.05 | 0.001 | Cases |
| 620.42 | 0.004 | 0.0003 | Controls |
| 630.47 | 0.03 | 0.007 | Cases |
| 703.56 | 0.02 | 0.1 | Controls |
| 714.62 | 0.07 | 0.002 | Controls |
| 724.52 | 0.0007 | 0.04 | Controls |
| 778.54 | 0.005 | 0.09 | Controls |
| 766.57 | 0.02 | 0.07 | Controls |
| 799.66 | 0.1 | 0.05 | Controls |
| 820.73 | 0.07 | 0.02 | Cases |
| 822.75 | 0.03 | 0.01 | Cases |
| 824.62 | 0.02 | 0.01 | Cases |
| 842.61 | 0.02 | 0.007 | Cases |
| 846.75 | 0.01 | 0.002 | Cases |
| 848.77 | 0.02 | 0.004 | Cases |
| 850.78 | 0.03 | 0.01 | Cases |
| 862.78 | 0.007 | 0.007 | Cases |
| 860.77 | 0.01 | 0.006 | Cases |
| 864.61 | 0.001 | 0.08 | Cases |
| 881.74 | 0.0005 | 0.1 | Cases |
| 886.78 | 0.02 | 0.01 | Cases |
| 888.80 | 0.01 | 0.008 | Cases |
| 890.81 | 0.005 | 0.003 | Cases |
| 912.76 | 0.005 | 0.05 | Cases |
| 930.84 | 0.01 | 0.01 | Cases |

Chemical Characterization of the Validated AD Diagnostic Lipid Biomarkers

Tandem MS studies were performed on all 35 confirmed, replicating lipid biomarkers to chemically characterize them. The exact mass, elemental composition, lipid class and molecular components were successfully determined for most of the confirmed lipid biomarkers. The assigned class and identified features of these markers are provided in Table 4. The rationale for the structural chemical assignments of the validated markers is explained hereafter and also summarized in Table 4.

TABLE 4

Chemical characterization of the lipid biomarkers from Table 3

| m/z | Exact mass | Adduct | Elemental composition | Class | Possible identity |
|---|---|---|---|---|---|
| 229.1 | 229.14 | | $C_{12}H_{21}O_4^+$ | Novel Lipid | |
| 430.4 | 430.38 | $M^+$ | $C_{29}H_{50}O_2^+$ | Sterol | Vitamin E |
| 488.4 | 488.39 | $M + NH_4^+$ | $C_{27}H_{50}O_6 + NH_4^+$ | Triacylglycerols | TG-8:0/8:0/8:0 |
| 496.3 | 496.33 | $M + H^+$ | $C_{24}H_{50}NO_7P + H^+$ | Lysophosphocholines | LysoPC 16:0 |
| 514.4 | 514.38 | | | | — |
| 522.3 | 522.35 | $M + H^+$ | $C_{26}H_{52}NO_7P + H^+$ | Lysophosphocholines | LysoPC 18:1 |
| 577.5 | 577.51 | $M^+$ | $C_{37}H_{69}O_4^+$ | Diacylglycerol | |
| 601.5 | 601.52 | $M^+$ | $C_{39}H_{69}O_4^+$ | Diacylglycerol | |
| 603.5 | 603.53 | $M^+$ | $C_{39}H_{71}O_4^+$ | Diacylglycerol | |
| 602.4 | 602.44 | | $C_{44}H_{58}O^+$ | Novel Lipid | |
| 610.5 | 610.53 | | $C_{41}H_{70}O_3^+$ | Novel Lipid | |
| 620.4 | 620.42 | | $C_{43}H_{56}O_3^+$ or $C_{47}H_{56}$ | Diacylglycerol? | |
| 630.4 | 630.47 | | $C_{46}H_{62}O^+$ | Novel Lipid | |
| 703.5 | 703.56 | $M + H^+$ | $C_{43}H_{76}N_2O_6 + H^+$ | Sphingomyelins | SM(d18:1/16:0) or SM(d16:1/18:0) |
| 714.6 | 714.61 | $M + NH_4^+$ | $C_{49}H_{76}O_2 + NH_4^+$ | Cholesterol esters | C22:6 cholesterol ester |
| 724.5 | 724.52 | $M + H^+$ | $C_{41}H_{74}NO_7P + H^+$ | Glycerophosphatidylethanolamines | PE(16:0p/20:4) |
| 778.5 | 778.57 | $M + H^+$ | $C_{45}H_{80}NO_7P + H^+$ | Glycerophosphatidylethanolamines | PE(18:0p/22:5) |
| 766.6 | 766.57 | $M + H^+$ | $C_{44}H_{80}NO_7P + H^+$ | Glycerophosphocholines | PC(O-16:1/20:4) |
| 799.6 | 799.66 | $M + H^+$ | $C_{46}H_{91}N_2O_6P + H^+$ | Sphingomyelins | SM(d17:1/24:1) or SM(d18:2/23:0) |
| 820.7 | 820.73 | $M + NH_4^+$ | $C_{51}H_{94}O_6 + NH_4^+$ | Triacylglycerols | TG-16:0/16:1/16:1 |
| 822.7 | 822.75 | $M + NH_4^+$ | $C_{51}H_{96}O_6 + NH_4^+$ | Triacylglycerols | TG-16:0/16:0/16:1 |
| 824.6 | 824.61 | $M + H^+$ | $C_{47}H_{86}NO_8P + H^+$ | Glycerophosphocholines | PC(39:4) |
| 842.6 | 842.61 | $M + H^+$ | $C_{46}H_{84}NO_{10}P + H^+$ | Glycerophosphocholines | PC(18:0/20:4) + OOH |
| 846.7 | 846.75 | $M + NH_4^+$ | $C_{53}H_{96}O_6 + NH_4^+$ | Triacylglycerols | TG-16:0/16:1/18:2 |
| 848.7 | 848.77 | $M + NH_4^+$ | $C_{53}H_{98}O_6 + NH_4^+$ | Triacylglycerols | TG-16:0/16:1/18:1 |
| 850.7 | 850.78 | $M + NH_4^+$ | $C_{53}H_{100}O_6 + NH_4^+$ | Triacylglycerols | TG16:0/16:0/18:1 |
| 862.7 | 862.78 | $M + NH_4^+$ | $C_{54}H_{100}O_6 + NH_4^+$ | Triacylglycerols | TG16:0/17:0/18:2 |
| 860.7 | 860.77 | $M + NH_4^+$ | $C_{54}H_{98}O_6 + NH_4^+$ | Triacylglycerols | TG16:1/17:1/18:1 |
| 864.6 | 864.61 | $M + H^+$ | $C_{49}H_{86}NO_9P + H^+$ | Oxidized Glycerophosphocholines | PC-$C_{49}H_{84}NO_8P$ + OH + $H^+$ |
| 881.7 | 881.74 | $M + H^+$ | $C_{56}H_{100}O_6 + H^+$ | Triacylglycerols | TG-16:0/18:0/20:5 |
| 886.7 | 886.78 | $M + NH_4^+$ | $C_{56}H_{100}O_6 + NH_4^+$ | Triacylglycerols | TG-17:0/18:1/18:3 |
| 888.8 | 888.80 | $M + NH_4^+$ | $C_{56}H_{102}O_6 + NH_4^+$ | Triacylglycerols | TG-17:0/18:1/18:2 |

TABLE 4-continued

Chemical characterization of the lipid biomarkers from Table 3

| m/z | Exact mass | Adduct | Elemental composition | Class | Possible identity |
|---|---|---|---|---|---|
| 890.8 | 890.81 | M + $NH_4^+$ | $C_{56}H_{104}O_6$ + $NH_4^+$ | Triacylglycerols | TG-17:0/18:0/18:2 |
| 912.7 | 912.76 | M + $NH_4^+$ | $C_{56}H_{98}O_7$ + $NH_4^+$ | Oxidized Triacylglycerols | 18:1/18:2/18:2 epoxide |
| 930.8 | 930.84 | M + $NH_4^+$ | $C_{59}H_{108}O_6$ + $NH_4^+$ | Triacylglycerols | TG-18:1/18:2/20:0 |

The fragmentation results are explained as follows:

Tandem MS studies on biomarker m/z 430.4 produced fragments at m/z 165 and m/z 205 consistent with the known fragmentation pattern of vitamin E. Based additionally on additional peaks in the broader fragmentation spectrum and on its putative elemental composition ($C_{29}H_{50}O_2^+$) as determined by exact mass studies, this lipid was completely consistent with its being vitamin E.

Fragmentation spectra of the markers with m/z 496.3 and 522.3 displayed a prominent peak at m/z 184.07 corresponding to a phosphocholine moiety. Fragmentation to patterns indicating neutral losses from the parent precursor ion suggested fatty acids present in the molecule. The fatty acid constituents were determined by comparing the theoretical fragments generated by the Lipid MS predictor feature of Lipid Maps with the experimentally produced fragments from the targeted biomarker. Elemental compositions were also predicted by exact mass studies. These peaks were both classified as lysophosphatidylcholines (LPC). The markers with m/z 496.3 and 522.3 were likely to be LPC-16:0 and LPC-18:1.

The elemental composition of marker m/z 577.5 was predicted to be $C_{37}H_{69}O_4^+$. This species is likely a diacylglycerol (DAG) arising from the neutral loss of a fatty acid from a triacylglycerol. However, it may potentially arise from the cleavage of the head group from a parent phospholipid (i.e. M+H+− head group), such as a glycerophosphoserine, glycerophosphoethanolamine, or glycerophosphoglycerol. The product ion peaks at m/z 265 and m/z 239 were also observed and concluded to be acylium ions ($RCO^+$) for 18:1 and 16:0 fatty acid substituents.

Similarly, the elemental compositions of markers m/z 601.5 and m/z 603.5 were proposed to be $C_{39}H_{69}O_4^+$ and $C_{39}H_{71}O_4^+$. These are also predicted to be DAGs arising from the neutral loss of a fatty acid from a TAG or possibly from the removal of the head group from a glycerophosphoserine, glycerophosphoethanolamine, glycerophosphoglycerol, or glycerophosphatidylcholine and appear to represent the remaining two fatty acids attached to a glycerol backbone. Additionally, the acylium ions observed in the $MS^2$ spectrum of the precursor ion m/z 601.5 were consistent with 18:1 (m/z 265) and 18:2 (m/z 263). Likewise, the fragmentation spectrum of the marker with m/z 603.5 presented peaks consistent with acylium ions from 18:1 (m/z 265) and 18:1 (m/z 265) fatty acids.

The markers with m/z 229.1, 602.4, 610.5, 620.4, and 630.4 were indicative of lipids, but with tandem MS fragmentation patterns and fragments not previously described. Their predicted elemental compositions, based on exact mass studies, are summarized in Table 4 above.

A dominant peak at m/z 184.06 was also displayed in the $MS^2$ spectra of markers with m/z 703.5 and 799.6, indicating a phosphocholine containing species. Therefore, the fragmentation spectra of the markers with m/z 703.5 and m/z 799.5 were most consistent with and were predicted to be sphingomyelins (SM) (for 703.5; SM (d 18:1/16:0) or SM (d16:1/18:0)) and (for 799.5; SM (d 18:2/23:0) or SM (d 17:1/24:1)).

Fragmentation studies applied to the marker m/z 714.6 resulted in a product fragment ion m/z 369.4. This same fragment is known to be characteristic of cholesterol esters. These specific fragmentation results suggested it to be a cholesterol ester of docosahexaenoic acid (22:6).

The markers with m/z 724.5 and m/z 778.5 were very likely glycerophosphoethanolamines (GPETn) as indicated by neutral loss of 141 from the parent ion with fragmentation. MS/MS spectra of m/z 724.5 displayed product ions at m/z 364 and m/z 361, consistent with being a 16:0p fatty acid group at the sn-1 position and a 20:4 fatty acid at sn-2 position. Its putative identification (16:0p/20:4) GPETn was also consistent with its elemental composition of $C_{41}H_{74}NO_7P+H^+$. Similarly, fragmentation of the marker with m/z 778.5 yielded product ions at m/z 392 and m/z 387, potentially indicating the presence of an 18:0p fatty acyl group at sn-1 position and a 22:5 acyl group at sn-2 position. Based on prior studies, the lipid with m/z 778.5 was predicted to be (18:0p/22:5) GPETn with an elemental composition of $C_{45}H_{80}NO_7P+H^+$.

A product ion at m/z 184.06 was also observed in the fragmentation spectra of markers with m/z 766.6, and 842.6 indicating they are glycerophosphocholines. Based on the $MS^2$ fragmentation pattern, Lipid Maps and exact mass studies, these results were most consistent with the m/z 766.6 being PC (0-16:1/20:4). The marker with m/z 842.6 displayed fragment ions at m/z 808.6 and m/z 824.6 corresponding to loss of hydrogen peroxide ($H_2O_2$) and water. An additional fragment ion at m/z 524.3 was also observed, indicating the presence of a C18:0 fatty acid. Therefore, the marker m/z 842.6 is predicted to be a protonated oxidized PC having a hydroperoxide group attached to PC (18:0/20:4).

The markers with m/z 824.6 and m/z 864.6 overlapped a peak adjacent to them. These could not be fully mass resolved using the instrument configuration employed in the present study and hence the fragmentation spectrum likely involved fragments from both overlapping peaks. Although, their fragmentation spectrum displayed a product ion at m/z 184.06 indicating a phosphocholine group, it was not conclusively determined as to which precursor peak, or whether both precursor peaks, was its source. This problem can be resolved with an instrument having a higher mass accuracy.

A number of peaks, e.g. those with m/z 488.3, 820.7, 822.7, 846.7, 848.7, 850.7, 860.7, 862.7, 886.7, 888.8, 890.8, 912.7, and 930.8 were highly likely to be ammoniated adducts of triacyglycerols (TAGs). A product ion representing the neutral loss of 17 was found for each and represents ammonia loss, consistent with TAGs readily forming ammonium adducts, i.e. the precursor ion was ammoniated (M+NH+) and ammonia was lost upon collision. The species with m/z 881.7 was found to be the protonated form (M+H+)

of a TAG. The combinations of fatty acids were predicted by observing the neutral loss of acylium ions from the precursor ion but absolute assignment is not possible in the absence of standards. The predicted fatty acid components for all the TAGs are provided in Table 4 above.

The species with m/z 912.8 displayed fragment ions at m/z 599.5, m/z 601.6, and m/z 615.5 corresponding to diacylglycerol fragments of $(18:2/18:2)^+$, $(18:2/18:1)^+$, and $(18:1/18:2_{epoxide})^+$. Therefore, marker m/z 912.8 was predicted to be an epoxide of 18:1/18:2/18:2 $(OLL_{ep})+NH^+$.

Figure 1A:
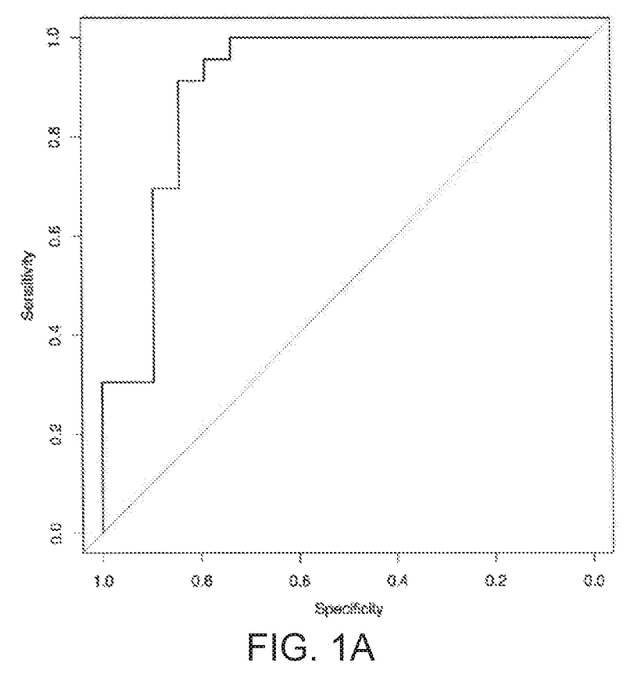
FIG. 1A is a representation of data in accordance with one aspect of the present disclosure.
Figure 1B:
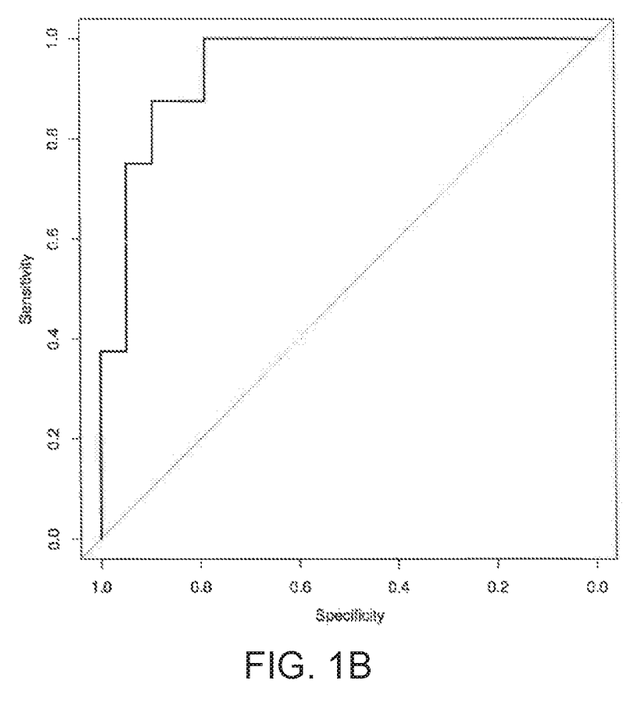
FIG. 1B is a representation of data in accordance with another aspect of the present disclosure.
Figure 1C:
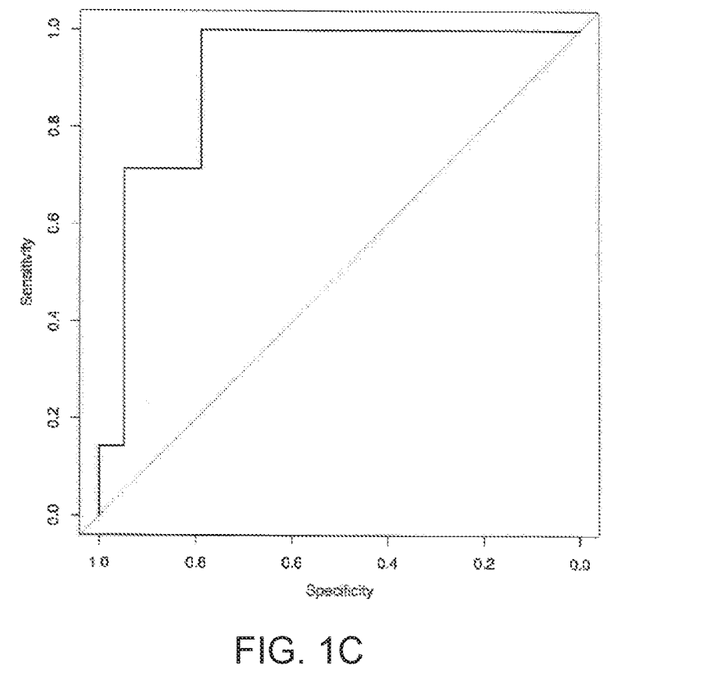
FIG. 1C is a representation of data in accordance with another aspect of the present disclosure.
Figure 1D:
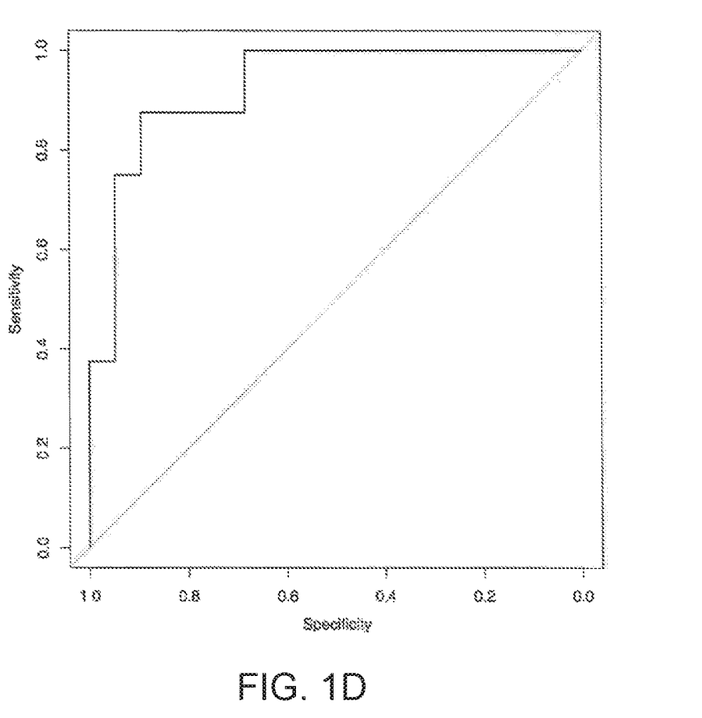
FIG. 1D is a representation of data in accordance with another aspect of the present disclosure.

Modeling of Multi-Marker Sets of the Verified Diagnostic AD Biomarkers to Increase their Ability to Classify AD Subjects Statistical modeling was performed on the 35 validated markers to develop combination sets or multimarker panels with higher diagnostic ability. Several panels using combinations of 4-9 markers were found to have AUCs>0.80. Modeling by means of Bayesian Lasso Probit Regression analysis was performed on controls versus all AD subjects and then on controls versus individual AD stage or CDR. These results are summarized in Table 5 and the individual receiver operator characteristic curves (ROC curves) are shown in FIGS. 1A-1D. In further detail with respect to FIGS. 1A-1D, these figures illustrate optimized combinations of diagnostic serum lipid biomarker sets for binary classification of AD subjects versus controls. Receiver operator characteristic curves (ROC) were generated by a Bayesian Lasso Probit Regression model. FIG. 1A illustrates the ROC curve for any stage AD versus control, which included 9 lipid biomarkers having mass to charge ratios of 229.1, 514.4, 602.4.610.5, 620.4, 630.5, 778.5, 799.7, and 824.6. The AUC was 0.904 with a sensitivity of ~91% at a specificity of 84%. FIG. 1B illustrates the ROC curve for CDR 0.5 vs controls and included biomarkers having mass to charge ratios of 229.1, 430.4, 514.4, 602.4, 610.5, 620.4, 778.5, 850.8, and 864.6. The AUC was 0.94 with a sensitivity of ~100% at a specificity of ~79%. FIG. 1C illustrates the ROC curve for CDR 1 vs controls and included biomarkers having mass to charge ratios of 430.4, 514.4, 602.4, 620.4, 630.5, 714.6, 766.6, 778.5, and 824.6. The AUC was 0.91 with a sensitivity of ~1.00% at a specificity of ~79%. FIG. 1D illustrates the ROC curve for CDR 2 vs controls and included biomarkers having mass to charge ratios of 229.1, 514.4, 620.4, 630.5, 778.5, and 842.7. The AUC was 0.93 with a sensitivity of ~88% at a specificity of ~90%.

Thus, promising sets of markers that provided high sensitivities and high specificities were found for the group of AD subjects that included all cases as well as for the individual stages of disease as suggested by the clinical dementia rating (CDR). These results are summarized in Table 5. With respect to the data depicted in Table 5, there were 9 markers in the set of CTL vs All AD, 9 markers in the set of CTL vs AD CDR 0.5, 9 markers in the set of CTL vs CDR 1 and 6 markers in the set of CTL vs AD CDR 2. Binary comparisons used Bayesian Lasso Probit Regression Classification Models.

TABLE 5

Optimized verified biomarker combinations for controls versus any stage AD or versus individual AD CDR stage.

| Model | AUC | Classification Rate | Sensitivity | Specificity | Threshold |
|---|---|---|---|---|---|
| CTL vs All AD | 0.904 | 0.88 | 0.91 | 0.84 | 0.52 |
| CTL vs AD CDR 0.5 | 0.941 | 0.85 | 1.0 | 0.79 | 0.47 |

TABLE 5-continued

Optimized verified biomarker combinations for controls versus any stage AD or versus individual AD CDR stage.

| Model | AUC | Classification Rate | Sensitivity | Specificity | Threshold |
|---|---|---|---|---|---|
| CTL vs AD CDR 1 | 0.910 | 0.85 | 1.0 | 0.79 | 0.46 |
| CTL vs AD CDR 2 | 0.928 | 0.89 | 0.88 | 0.90 | 0.54 |

Note:
CTL: control subjects, AD: Alzheimer's disease, CDR: Clinical dementia, rating.

The binary classification models suggested that some markers appeared to change proportional to disease stage. As such, these markers could be potentially useful in staging AD. To test this, a Bayesian Lasso Probit Ordinal regression model that included n-fold cross validation was used. This optimized set of biomarkers, which correctly assigned disease stage to 71% of subjects, is summarized in Table 6. With respect to the data depicted in Table 6, this model had a classification rate of 0.714 and p-value 0.0005. A positive coefficient estimate indicates that the marker increased in abundance with an increase in disease severity whereas a negative coefficient estimate changed inversely with disease stage.

TABLE 6

Set of optimized verified biomarkers developed to stage AD. A Bayesian Lasso Probit Ordinal Regression Model is summarized.

| Marker | {m/z} | Coefficient Estimate | Lower Boundary | Upper Boundary |
|---|---|---|---|---|
| Biomarker 1 | 229.13 | −0.126 | −0.557 | 0.161 |
| Biomarker 2 | 514.38 | 0.117 | −0.205 | 0.593 |
| Biomarker 3 | 602.40 | 0.105 | −0.207 | 0.556 |
| Biomarker 4 | 620.42 | −0.407 | −1.037 | 0.030 |
| Biomarker 5 | 630.47 | 0.092 | −0.229 | 0.519 |
| Biomarker 6 | 703.56 | 0.122 | −0.163 | 0.552 |
| Biomarker 7 | 724.52 | −0.080 | −0.429 | 0.180 |
| Biomarker 8 | 778.54 | −0.175 | −0.693 | 0.111 |
| Biomarker 9 | 799.66 | −0.080 | −0.417 | 0.180 |
| Biomarker 10 | 824.60 | 0.209 | −0.096 | 0.682 |
| Biomarker 11 | 842.66 | 0.088 | −0.183 | 0.443 |

Figure 2:
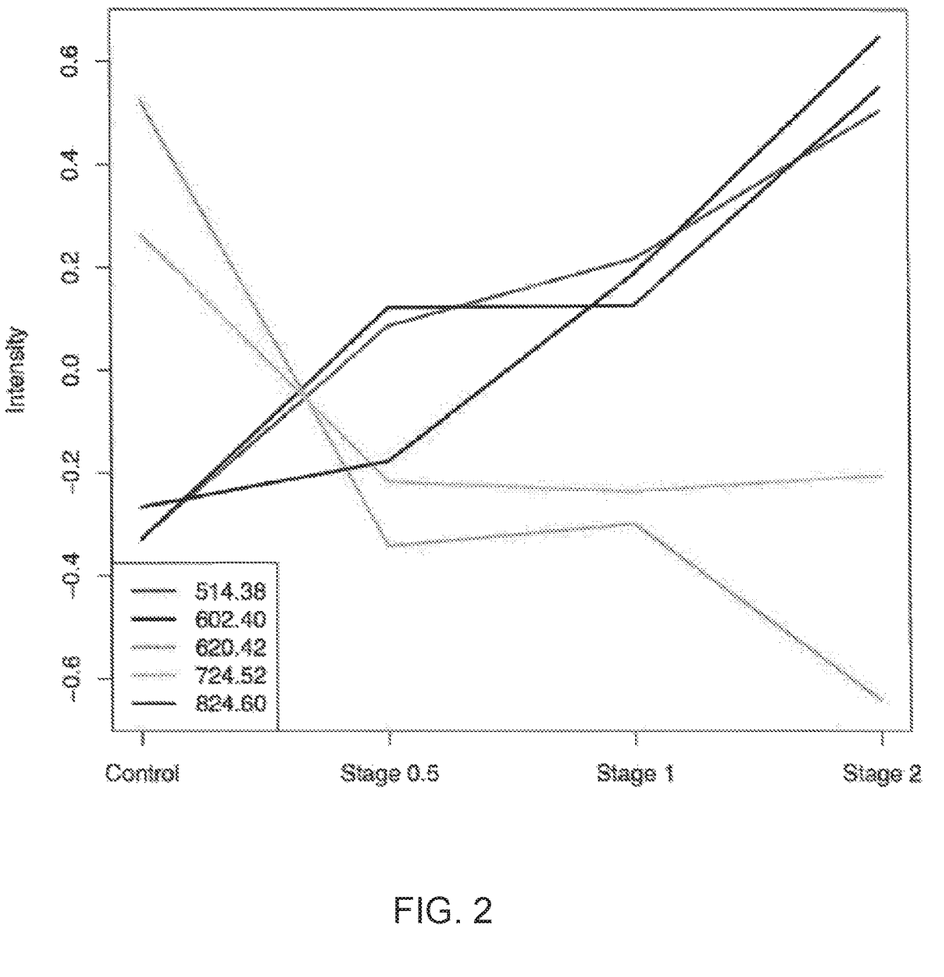
FIG. 2 is a representation of data in accordance with another aspect of the present disclosure.

Representative markers, included in the optimized set, are shown in FIG. 2. Specifically, FIG. 2 illustrates serum lipid biomarkers having nearly monotonic relationships with disease stage. The y-axis plots the mean peak abundance for a specific lipid marker versus the disease stage as indicated by AD CDR rating on the x-axis. Five biomarkers that demonstrated strong positive or negative correlations with AD stage are plotted (m/z 514.4, 602.4, 620.4, 724.5, 824.6 (listed in inset)). The overall Bayesian Lasso Probit Ordinal Regression model had a classification rate of 0.71, p=0.0005.

To predict future performance, a 10-fold internally validated Bayesian Lasso Probit Regression analysis was carried out for all AD cases versus controls and then each stage of the disease or CDR versus controls. This conservative approach estimated that biomarker future performance, while less sensitive or specific, nonetheless continued to identify the majority of AD cases correctly, even by stage. These results are summarized in Table 7. With respect to the data depicted in Table 7, there were 9 markers in the set to of CTL vs All AD, 9 markers in the set of CTL vs AD CDR 0.5, 9 markers in the set of CTL vs CDR 1, and 6 markers in the set of CTL vs AD CDR 2 Binary comparisons used 10-fold cross validated Bayesian Lasso Probit Regression Classification Models.

TABLE 7

Predicted future performance of AD biomarker sets using cross validated performance estimates of the previous verified biomarker sets considered in Table 5

| Model | AUC | Classification Rate | Sensitivity | Specificity |
|---|---|---|---|---|
| CTL VS All AD | 0.762 | 0.76 | 0.78 | 0.74 |
| CTL vs AD CDR 0.5 | 0.822 | 0.78 | 0.50 | 0.90 |
| CTL vs AD CDR 1 | 0.632 | 0.63 | 0.14 | 0.84 |
| CTL vs AD CDR 2 | 0.763 | 0.78 | 0.88 | 0.74 |

Note:
CTL: control subjects, AD: Alzheimer's disease, CDR: Clinical dementia rating.

Therefore, this study employs a global lipidomic approach using direct infusion mass spectrometry to interrogate serum. Direct infusion mass spectrometry using ESI-MS has been shown to be as quantitative and faster than other MS analyses and useful in the analysis of the lipids in the extracts of biological samples. It allows for the screening of many individual lipids from diverse lipid classes. This study was conducted to determine if lipid biomarkers existed that discriminated AD cases from controls, especially subjects with very early stage AD, and to determine whether such markers would provide further insight into AD pathology.

As is apparent from the results described above, this approach led to the discovery and confirmation of 35 lipid biomarkers differentiating any stage of AD from controls across two independent studies. Alterations in the levels of lipid species belonging to various lipid classes was observed, including sterols, sphingomyelins (SM), glycerophosphocholines (PC), glycerophosphoethanolamines (PE), lysophosphocholines (LPC), diacylglycerols (DG) and triacylglycerols (TAG). Combinations of these markers provided panels with ROC curves having AUCs greater than 0.90 for all-stage AD. The best of these provided a sensitivity of 91% with a specificity of 84% for all stages of AD collectively. The ability of combinations of these same 35 markers to identity subjects with a particular stage of AD versus controls was also modeled. The best models provided sensitivities approaching or above 90% for CDR 0.5, 1, or 2 individually with specificities of at least about 80%. While the number of subjects in these subgroups was small, the results nonetheless suggest strongly that serum lipid biomarkers are present that diagnose AD, even very early stage AD.

Thus, it was demonstrated that direct infusion mass spectrometry was reasonably effective in a broad, untargeted analysis of the serum lipidome. It allowed fast, uncomplicated, high throughput and semiquantitative analysis of more than 1000 lipids. It resulted in reproducible discrimination of AD cases from controls.

With respect to specific, identified markers, one marker with m/z 430.4 was consistent with its being vitamin E. Its levels were found to be significantly increased in the serum samples of AD cases.

Two markers with m/z 496.3 and m/z 522.3 found to be higher in AD cases belonged to the class of lysophosphocholines (LPC). Neurodegeneration, a key feature of AD, results in the breakdown of cell membranes potentially increasing the release of membrane lipids into the circulation. Also, activation of phospholipase $A_2$ ($PLA_2$), responsible for the enzymatic hydrolysis of the sn-2 fatty acyl group of phosphocholines leading to increased production of LPCs, was also increased in AD subjects. Furthermore, LPC produced through hydrolysis of PC by $PLA_2$ can be a precursor of platelet activating factor (PAF), which in turn can act as a mediator of inflammation. There is clear and strong evidence of inflammation in the brains of AD subjects. As such, alterations in levels of these markers may be explained by and potentially represent pathological events giving rise to higher levels of LPCs in AD cases.

Two markers with m/z 703.5 and m/z 799.6, found to be lower in AD subjects, were determined to be sphingomyelins (SM). SMs are metabolized to ceramides, which can play an important role in cell differentiation, proliferation, and apoptosis. Ceramides are also involved atherosclerosis.

Candidate biomarkers with m/z 724.5 and m/z 778.5 were decreased in AD cases. Both belonged to the class of PEs. Ethanolamine plasmalogen (PlsEtn), representing ~90% of all PEs, is highly enriched in white and grey matter of the human brain. PlsEtn provides a sheath for axons in white matter and acts as a source of lipid messengers participating in signal transduction in grey matter. Its deficiency in white matter likely contributes to myelin sheath defects and axonal dysfunction contributing to dementia in AD subjects. Plasmalogen deficiency in cerebral grey matter may result in synapse loss due to membrane instability, which may explain the reduced levels of PE in AD subjects in this study.

The candidate marker with m/z 842.6 was predicted to be an oxidized PC species having a hydroperoxide group attached to PC (18:0/20:4). It was found to be higher in AD cases. The increased oxidative stress observed in neurodegenerative disorders likely results in increased lipid oxidation and may possibly explain the higher levels of this marker among AD cases in this study. Similarly, the marker with m/z 912.7 was found to be an ammoniated adduct of an oxidized TAG and was higher in AD cases. AD is associated with increased levels of oxidative stress. F2-isoprostane, which is produced from polyunsaturated fatty acids as a result of free radical mediated peroxidation, can be higher in the brain and CSF of AD subjects.

Several other candidate lipid markers, those with m/z 820.7, 822.7, 846.7, 848.7, 850.7, 860.7, 862.7, 881.7, 886.7, 888.8, 890.8, and 930.8, all belong to the class of triacylglycerols (TAGs) and were found to be higher in AD cases. Elevated triglyceride levels can precede amyloid deposition in AD subjects.

Of course, it is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been described above with particularity and detail in connection with what is presently deemed to be the most practical embodiments of the disclosure, it will be apparent to those of ordinary skill in the art that numerous modifications, including, but not limited to, variations in size, materials, shape, form, function and manner of operation, assembly and use may be made without departing from the principles and concepts set forth herein.

The invention claimed is:
1. A method of determining the presence of Alzheimer's disease in a subject, comprising:
   detecting Biomarker 4 in a biological medium obtained from the subject;
   determining presence of Alzheimer's Disease in the subject from the presence of Biomarker 4; and
   treating the subject for Alzheimer's disease by administering a medication or treatment, wherein Biomarker 4 has a molecular formula of $C_{43}H_{56}O_3^+$ or $C_{47}H_{56}$ and has a mass-to-charge ratio (m/z) of 620.4.

2. The method of claim 1, wherein the biological medium is a biological fluid.

3. The method of claim 1, wherein detecting in the biological medium further includes detecting using mass spectrometry.

4. The method of claim 1, wherein the medication comprises a cholinesterase inhibitor, memantine, an anti-amyloid beta antibody, an antitau antibody, or a combination thereof.

5. The method of claim 1, wherein the treating comprises neurostimulation.

6. The method of claim 1, wherein treating the subject for Alzheimer's disease begins at a clinical dementia rating (CDR) of 0.5.

7. A method of determining the presence of Alzheimer's disease in a subject, comprising:
    detecting Biomarker 11 in a biological medium obtained from the subject;
    determining presence of Alzheimer's Disease in the subject from the presence of Biomarker 11; and
    treating the subject for Alzheimer's disease by administering a medication or treatment,
    wherein Biomarker 11 has a molecular formula of $[C_{46}H_{84}NO_{10}P]+H^+$ or $[C_{47}H_{86}NO_8P]+H^+$ and has a mass-to-charge ratio (m/z) of 842.6.

8. The method of claim 7, wherein the biological medium is a biological fluid.

9. The method of claim 7, wherein detecting in the biological medium further includes detecting using mass spectrometry.

10. The method of claim 7, wherein the medication comprises a cholinesterase inhibitor, memantine, an anti-amyloid beta antibody, an antitau antibody, or a combination thereof.

11. The method of claim 7, wherein the treating comprises neurostimulation.

12. The method of claim 7, wherein treating the subject for Alzheimer's disease begins at a clinical dementia rating (CDR) of 0.5.

13. A method of determining the presence of Alzheimer's disease in a subject, comprising:
    detecting Biomarker 3 in a biological medium obtained from the subject;
    determining presence of Alzheimer's Disease in the subject from the presence of Biomarker 3; and
    treating the subject for Alzheimer's disease by administering a medication or treatment,
    wherein Biomarker 3 has a molecular formula of $C_{44}H_{58}O^+$ and a mass-to-charge ratio of 602.4.

14. The method of claim 13, wherein the biological medium is a biological fluid.

15. The method of claim 13, wherein detecting in the biological medium further includes detecting using mass spectrometry.

16. The method of claim 13, wherein the medication comprises a cholinesterase inhibitor, memantine, an anti-amyloid beta antibody, an antitau antibody, or a combination thereof.

17. The method of claim 13, wherein the treating comprises neurostimulation.

18. The method of claim 13, wherein treating the subject for Alzheimer's disease begins at a clinical dementia rating of (CDR) 0.5.

* * * * *